United States Patent
Pronovost et al.

[11] Patent Number: 5,804,452
[45] Date of Patent: Sep. 8, 1998

[54] ONE STEP URINE CREATININE ASSAYS

[75] Inventors: Alan Pronovost, San Diego; Jan Pawlak, Encinitas, both of Calif.

[73] Assignee: Quidel Corporation, San Diego, Calif.

[21] Appl. No.: 431,706

[22] Filed: Apr. 27, 1995

[51] Int. Cl.⁶ .................................................. G01N 33/558
[52] U.S. Cl. ........................ 436/514; 436/518; 436/525; 436/538; 436/541; 436/817; 435/7.1; 435/69.4; 435/69.7; 435/961; 435/962; 435/970; 435/973; 422/56; 422/57; 530/350; 530/806; 530/807
[58] Field of Search ...................... 422/56–57; 435/7.1, 435/7.92–7.95, 69.1, 69.4, 69.7, 961, 962, 970, 973; 436/518, 817, 525, 514, 538, 541, 814; 530/350, 806, 807

[56] References Cited

U.S. PATENT DOCUMENTS

| | | | |
|---|---|---|---|
| 4,446,233 | 5/1984 | Auditore-Hargreaves et al. | 435/7.9 |
| 4,479,895 | 10/1984 | Auditore-Hargreaves | 260/112 B |
| 4,578,361 | 3/1986 | Siedel et al. | 436/547 |
| 4,675,382 | 6/1987 | Murphy | 530/350 |
| 4,740,364 | 4/1988 | Hodges | 424/9 |
| 4,745,055 | 5/1988 | Schenk et al. | 435/7.9 |
| 4,780,422 | 10/1988 | Mitani et al. | 436/524 |
| 4,861,711 | 8/1989 | Friesen et al. | 435/7.9 |
| 4,943,522 | 7/1990 | Eisinger | 436/512 X |
| 4,999,285 | 3/1991 | Stiso | 435/7.9 |
| 5,120,643 | 6/1992 | Ching et al. | 435/7.92 |
| 5,141,850 | 8/1992 | Cole et al. | 436/525 |
| 5,156,952 | 10/1992 | Litman et al. | 435/7.91 |
| 5,223,220 | 6/1993 | Fan et al. | 422/58 |
| 5,283,176 | 2/1994 | Sato et al. | 435/7.1 |
| 5,310,646 | 5/1994 | Whitley | 435/4 |
| 5,370,135 | 12/1994 | Dullien | 128/89.8 |
| 5,385,847 | 1/1995 | Yip et al. | 436/534 |
| 5,415,994 | 5/1995 | Imrich et al. | 435/5 |
| 5,416,000 | 5/1995 | Allen et al. | 435/7.92 |

FOREIGN PATENT DOCUMENTS

| | | | |
|---|---|---|---|
| 0 252 368 | 1/1988 | European Pat. Off. | |
| 0 281 000 | 9/1988 | European Pat. Off. | 435/21 |
| 0 409 345 | 1/1991 | European Pat. Off. | 435/25 |
| 0 546 390 | 6/1993 | European Pat. Off. | 435/4 |
| 2102568 | 2/1983 | United Kingdom | 435/4 |
| 9201226 | 1/1992 | WIPO | 422/56 |
| 9212428 | 7/1992 | WIPO | 422/56 |
| 9218866 | 10/1992 | WIPO | 435/9.73 |

*Primary Examiner*—Carol A. Spiegel
*Attorney, Agent, or Firm*—Townsend and Townsend and Crew, LLP

[57] ABSTRACT

The present invention provides devices and methods for the detection of creatinine in biological fluids using lateral flow methodologies. The invention is particularly useful in providing one step creatinine assays for correcting urinary steroid hormone assays.

8 Claims, 2 Drawing Sheets

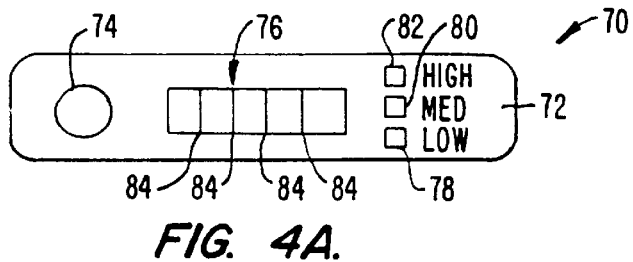
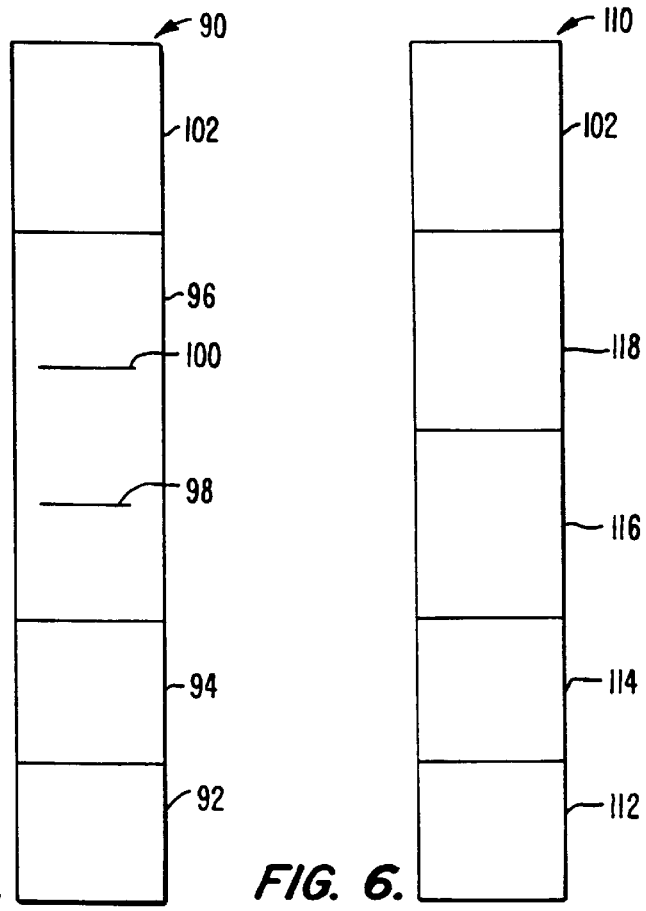
FIG. 4A.
FIG. 4B.
FIG. 5.
FIG. 6.

ONE STEP URINE CREATININE ASSAYS

BACKGROUND OF THE INVENTION

The present invention relates generally to devices and methods for detection of analytes in biological samples. More specifically, the present invention provides devices and methods for detection of creatinine in urine samples.

Detection of creatinine in urine is useful in a number of diagnostic applications. Creatinine is one of the byproducts of protein metabolism. Under normal conditions it is present in the blood and is excreted as a final metabolite in the urine. Urine creatinine levels are routinely used as part of kidney function diagnosis. In particular, altered creatinine levels in urine are indicative of kidney diseases such as acute or chronic nephritis, nephrosis, and the like.

Because normative values for creatinine excretion have been established, urine creatinine levels are also useful for correction of assays for other compounds (e.g., pancreatic amylase, steroid hormones and hormone metabolites) in urine. The measurement of urinary excretion of hormones offers advantages over direct measurement of plasma levels because the procedure is non-invasive and urine levels reflect average plasma levels over the time of collection. Urinary creatinine levels are used to document the adequacy of the urine collection for such assays. In particular, changes in renal function which influence rates of hormone excretion, can be corrected by measurement of creatinine in urine.

The first practical test for creatinine detection was the Jaffe method which is based on the reaction with picric acid in an alkaline solution. Other methods of detecting creatinine utilize various enzyme catalyzed reactions to produce a detectable product. Alternatively, antibodies specific for creatinine can be used.

Devices and methods are needed in the art which will provide simple and convenient detection of urinary creatinine.

In particular, assays which provide simultaneous correction for detection of urinary steroids, fertility hormones, or urinary proteins indicative of bone resorption and deposition would be desirable. In addition, the devices should be economical to produce and simply assembled. The present invention addresses these and other needs.

SUMMARY OF THE INVENTION

The present invention provides devices for determining creatinine levels in a sample. In certain embodiments, the devices comprise a matrix defining a flow path, a sample pad for receiving a fluid sample on the matrix, and an assay strip located downstream from the sample pad. The assay strip comprises a reagent pad, having a first reagent for detecting creatinine in the sample, and a detection zone located downstream from the reagent pad, the detection zone having a second reagent for the detection of creatinine in the sample. Application of a fluid sample to the sample pad results in flow of sample through the reagent pad to the detection zone, such that creatinine in the sample results in the accumulation of a detectable dye in the detection zone.

The sample pad of the devices may comprise means for removing compounds that interfere with the detection of creatinine, such as sarcosine oxidase immobilized on a plurality of beads or an anti-creatine antibody. Various compounds used for the detection of creatinine, including labeled creatinine complexes, may be placed on the reagent pad.

The present invention also provides devices for determining both target analyte and creatinine levels in a sample. These devices comprise first and second assay strips, such that creatinine in the sample results in the accumulation of a first detectable dye in the first assay strip and target analyte in the sample results in accumulation of a second detectable dye in the second assay strip. Typically, the target analyte is a urinary steroid, such as estrogen.

The invention further provides devices for correcting target analyte levels in a fluid sample from a patient. The devices comprise an assay strip comprising a labeled complex comprising a visible label bound to a target analyte conjugated to creatinine. The capture zone of the assay strips comprise a first region comprising a creatinine binding substance immobilized thereon and a second region comprising a target analyte binding substance immobilized thereon. If the level of creatinine is sufficient, there will be accumulation of the labelled complex in the second region of the capture zone.

The invention also provides methods of correcting target analyte levels in a fluid sample from a patient. The methods involve determining a creatinine level and a target analyte level in the sample using the devices of the invention. Typically, the fluid sample is a urine sample.

BRIEF DESCRIPTION OF THE DRAWINGS

FIG. 4A illustrates a device constructed in accordance with the principles of the invention.

FIG. 4B illustrates a color key used with the device illustrated in FIG. 4A.

FIG. 5 illustrates an assay strip of the present invention in which a label complex comprising a visible label bound to a target analyte conjugated to creatinine is used to correct target analyte concentrations. The assay strip includes a capture zone comprising a first region for detection of creatinine and a second region for detection of the target analyte.

FIG. 6 illustrates an assay strip similar to that illustrated in FIG. 5, except that the first region for detection of creatinine is a lawn of anti-creatinine antibodies and the second region for detection of the target analyte is a lawn of anti-estrogen antibodies.

DESCRIPTION OF THE PREFERRED EMBODIMENTS

Figure 1:
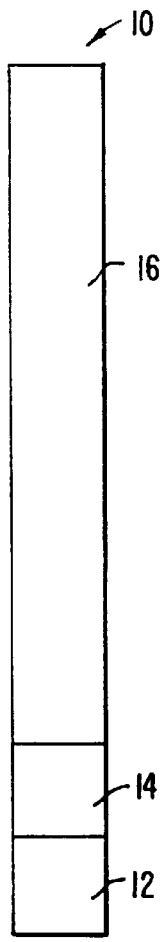
FIG. 1 illustrates an assay strip employed in devices constructed in accordance with the principles of the present invention.

The devices and methods of the present invention employ lateral flow methodology for detection of analytes such as creatinine and urinary steroids, fertility hormones and urinary proteins indicative of bone resorption or bone deposition. The samples are generally biological fluids. The biological fluid sample may be whole blood, plasma, serum, nasal secretions, sputum, salvia, urine, sweat, transdermal exudates, cerebrospinal fluid, or the like. Analytes in biological tissue samples may also be detected by homogenizing or otherwise liquefying the tissue sample. The sample, whether a fluid or liquified tissue, may be diluted with physiological buffers, such as physiological saline, to facilitate sample flow in the devices of the present invention. The devices are preferably used for the detection of analytes in urine.

The devices and methods of the present invention employ a matrix suitable for lateral flow assay techniques as generally described in U.S. Pat. Nos. 4,943,522; 4,861,711; 4,857,453; 4,855,240; 4,775,636; 4,703,017; 4,361,537; 4,235,601; 4,168,146; 4,094,647; European Patent Application Nos. 451,800; 158,746; 276,152; 306,772 and British Patent Application No. 2,204,398.

The devices of the present invention generally comprise a matrix defining a flow path; a sample receiving zone or sample pad for receiving the fluid sample on the matrix; and an assay strip located downstream from the sample pad. The assay strip comprises a reagent pad, comprising reagents useful for detection of creatinine, and a detection zone located downstream from the reagent zone, whereby application of the fluid sample to the sample receiving zone results in the accumulation of a detectable colored dye. The devices may have a single sample receiving zone that fluidly communicates with more than one assay strip that detect different compounds, e.g., creatinine and a steroid hormone. Alternatively, each assay strip may be able to detect a steroid hormone and creatinine. In some instances, the sample receiving zones may be present on the assay strips.

The matrix of the devices of the present invention will typically be capable of non-bibulous lateral flow. By "non-bibulous lateral flow" is meant liquid flow in which all of the dissolved or dispersed components of the liquid are carried at substantially equal rates and with relatively unimpaired flow laterally through or across the matrix, as opposed to preferential retention of one or more components as would occur, e.g., in materials capable of adsorbing or imbibing one or more components.

A representative non-bibulous matrix material is high density polyethylene sheet material. Polyethylene sheets of this type are available from commercial sources, such as by Porex Technologies Corp. of Fairburn, Ga., USA. Generally, the membrane has an open pore structure with a typical density, at 40% void volume, of 0.57 gm/cc and an average pore diameter of 1 to 250 micrometers, the average generally being from 3 to 100 micrometers. Usually the membrane pore diameter is about 0.2 to about 50 $\mu$m, although other pore diameters may be employed for different purposes. For example, a membrane having large pores may filter particulate from a sample and selectively allow the fluid and dissolved compounds in the sample to flow downstream.

The membranes are from a few mils (0.001 in) to several hundred mils in thickness, typically in the range of 5 mils to 200 mils. The membrane may be backed by a generally water impervious layer, or may be totally free standing. Free standing matrixes will generally be thicker since structural support for the device will be provided by the matrix. Other non-bibulous membranes, such as polyvinyl chloride, polyvinyl acetate, copolymers of vinyl acetate and vinyl chloride, polyamide, polycarbonate, nylon, glass fiber, orlon, polyester polystyrene, and the like, or blends can also be used.

Bibulous materials, such as untreated paper, nitrocellulose, derivatized nylon, cellulose and the like may also be used following processing to provide non-bibulous flow. Bibulous materials may also act as filtering mechanisms as described above. Alternatively, blocking agents may block the forces which account for the bibulous nature of bibulous membranes. Suitable blocking agents include whole or derivatized bovine serum albumin or albumin from other animals, whole animal serum, casein, and non-fat dry milk.

The matrix defines a flow path for fluids applied to the matrix. The flow path is the natural movement of fluids placed on the matrix. The matrix has a sample receiving zone or sample pad. The sample pad is the portion of the matrix to which the samples are applied. Generally, the sample pad will have a low analyte retention. Treatment of the sample pad to immobilize a protein-blocking reagent on the surface, if necessary, will typically provide low retention properties. This treatment also provides increased wetability and wicking action to speed the downstream flow of the sample. The sample receiving zone may also serve as a means for filtering particulate from the sample.

The present invention relates to the determination (qualitative or semiquantitative measurement) of creatinine in aqueous liquids, usually urine. Typically, the detection of creatinine is used as a calorimetric indicator to confirm that a urine sample is sufficiently concentrated for detection of other compounds, such as urinary steroids, fertility hormones and urinary proteins indicative of bone resorption or bone deposition. Examples of fertility hormones include estrogen, progesterone, and their metabolites such as estradiol, estrone, estriol, or pregnendiol glucuronide (PDG). Another analyte suitable for detection using the methods of the invention is pancreatic amylase. For instance, immunoassays can be used for assessing abnormal levels of pancreatic amylase in serum and urine which are indicative, for example, of pancreatitis, acute alcohol ingestion or poisoning, renal malfunction or advanced cystic fibrosis.

To illustrate the invention, the following discussion will focus on the detection of a particular steroid hormone, estrogen and naturally occurring estrogen metabolites, such as, estradiol, estrone, or estriol. Estrogen levels may be used for a number of purposes, such as determining periods of fertility, and the like. One of skill will recognize that the detection of creatinine using the methods of the invention can be used for the correction of assays for other analytes, as well.

Typically, the devices of the invention comprise a means for determining estrogen or estrogen metabolite levels in urine according to methods known in the art. Generally, the hormone will be determined on assay strips having a means for labeling the target hormone and a capture zone wherein the means for labeling the hormone from the sample may accumulate and be observed. Alternatively, labeled hormone conjugate may be use in a competitive assay as described below.

To determine urinary estrogen or other urinary steroid or hormone levels, a urine sample is applied to the sample pad of an assay strip. The sample pad may be applied drop wise or by dipping the sample receiving zone of the assay strip into the urine. Generally, urine samples are collected at the same time each day. It is advisable to test the first urine after arising as the first void levels of hormones are at their highest and most consistent urinary levels. Also, testing is more accurate if fluid intake is restricted for about 2 hours prior to collecting the sample. The urine sample may be tested up to 8 hours after collection, if refrigerated. Prior to testing the urine should be warmed to room temperature.

The sample pad may remove erythrocytes, leukocytes, and/or different hormones from the sample. Generally, removal is accomplished by immobilized antibody to the cells or hormones to be removed. The sample pad may also be constructed so as to act as a filter for cellular components in a sample.

The assay strips comprise a labelling zone and a capture zone. A means for labelling the target hormone is present in the labelling zone. A variety of labelling complexes may be employed in the devices. The labelling means contain labelling complexes that specifically bind to the respective target hormone in the sample. The labeling complexes are often a first target hormone binding substance bound to a visible label. In addition, as explained below, the hormone binding substance may be further conjugated to creatinine.

In the case of estrogen, labeling complexes employ an estrogen binding substance, e.g., anti-estrogen antibody or estrogen receptor bound to a label. The target hormones in the sample are indirectly labelled and thereby rendered identifiable by specifically binding to the corresponding labelling complex. The capture zone often contains an immobilized second hormone or its close analogue covalently attached to a macromolecular proteinaceous carrier (hormone hapten). The carrier may be intact or derivatized serum albumin or immunoglobulin from a variety of species, or a fragment thereof.

As explained above, a labelled immunoglobulin that specifically reacts with the target hormone may be the labelling means. The antigen-binding region of a specific immunoglobulin provides for specific binding of the target hormone in the sample. The immunoglobulins may be antibodies of any isotype, such as IgA, IgG, or IgM, Fab fragments, F(ab')$_2$ fragments, Fab' fragments, or the like. The immunoglobulins may be monoclonal or polyclonal and produced by methods as generally described in Harlow and Lane, *Antibodies, A Laboratory Manual* (Cold Spring Harbor Laboratory, 1988). The labelling complex is not immobilized to the labelling zone so that the fluid sample may solubilize or otherwise remove the labelling complexes into the fluid of the sample.

The receptors may be produced by methods of recombinant DNA technology or isolated from tissue by techniques such as affinity immunopurification as described in Sambrook et al., *Molecular Cloning, A Laboratory Manual* (Cold Spring Harbor Laboratory Press, 2d ed., 1989).

A variety of visible labels may be bound to the target hormone-binding substances. The labels may be soluble or particulate and may include dyed immunoglobulin binding substances, simple dyes or dye polymers, dyed latex beads, dye-containing liposomes (such as described in U.S. Pat. No. 4,695,554) dyed cells or organisms, or metallic, organic, inorganic, or dye sols. The labels may be bound to the hormone-binding substance by a variety of means that are well known in the art such as described in U.S. Pat. Nos. 4,863,875 and 4,373,932. In some embodiments of the present invention, the labels may be enzymes that can be coupled to a signal producing system, such as described in U.S. Pat. No. 4,366,241.

Because the target hormone labelling complexes contain a target hormone-binding substance and the labelling complexes are solubilized or dispersed into the sample, the target hormone in the sample is contacted and bound by the labelling complexes prior to entering the capture zone. In this manner, target hormones in the sample are indirectly labelled.

The test for steroid hormone or other analyte is based on a competitive principle. For instance, the hormone in the sample may compete for binding sites on a labelled hormone binding substance (e.g., antibody) with hormone immobilized on a specific test line in the capture zone. The amount of labelled antibody is adjusted so that even a very low amount of hormone in the sample will block the binding site and no colored specific line can be formed in the capture zone. Therefore, if two colored lines have appeared, the test can be interpreted as being negative. If only one colored line (the control line) has appeared, the test is positive and the sample contains steroid hormone. In addition, the labelled hormone binding substance may be linked to creatinine to provide for creatinine correction in the same device. A capture zone comprising a creatinine binding substance (e.g., anti-creatinine antibodies) can be used to determine if the creatinine levels are sufficient (see, e.g., FIG. 5).

The labeling complexes may be biotinylated or labeled with another ligand anti-ligand system to facilitate bound and free separation in a lateral flow assay format where in the absence of analyte the labeling complex will bind via its antibody to a first capture zone comprised of excess analyte bound to carrier protein but when the analyte is present, the analyte in the sample will bind the biotinylated antibody and bypass the first capture zone and will be bound by a second capture zone composed of an anti-ligand such as streptavidin, thus providing a positive readout for analyte as analyte concentration.

Immobilization of the hormone hapten will generally be accomplished by application of the target hormone binding substance to the capture zone in a suitable buffer, followed by non-specific blocking of surrounding areas with bovine serum albumin, non-fat milk, or the like. The assay strip may contain two capture zones. In this case, hormone binding substance which is not bound to the target hormone will bind to the first capture zone and to the second capture zone in the presence of target hormone.

As noted above, the devices of the invention which measure estrogen or other steroids or hormones in urine include assay strips for detection of creatinine for corrections to overcome biological variations and to confirm concentration of the urine sample. A number of assays can be used for the determination of creatinine in urine or plasma. For instance, the following sequence of reactions can be used:

(1) creatinine+water$\leftrightarrows$creatine
(2) creatine+water→urea+sarcosine
(3) sarcosine+oxygen+water→glycine+formaldehyde+hydrogen peroxide
(4) hydrogen peroxide+horseradish peroxidase (HRP) substrate→detectable dye.

These reactions are catalyzed by creatininase (EC 3.5.2.1.0), creatinase (EC 3.5.3.3), sarcosine oxidase (EC 1.5.3.1) and HRP (EC 1.11.1.7), respectively. In addition, sarcosine dehydrogenase (EC 1.5.99.1) can be used to catalyze reaction 3. For a description of these reactions see, U.S. Pat. No. 4,215,197.

Another assay format includes incubation of the sample with creatinine:NAD(P) oxidoreductase and NAD(P). The level of NAD(P)H, a product of this reaction, is then determined. Typically, NAD(P)H is detected by its ability to reduce tetrazolium salts. Thus, creatine is measured by the detection formazans (see, EPO 252 368).

Creatinine may also be enzymatically converted to N-methylhydantoin and ammonia by creatinine iminodehydrolase (EC 3.5.4.21). The ammonia is then calorimetrically detected. GB 2 102 568. This method requires correction for endogenous ammonia present in the sample.

Enzymes useful for the above assays are readily available. Creatininase and creatinase can be obtained commercially from a number of sources (e.g., Sigma, St. Louis, Mo.). Several species of each enzyme, isolated from various microbial sources, are described in U.S. Pat. Nos. 3,806,416 and 4,039,384. Any of the species can be used in the practice of this invention. The creatininase and the creatinase both obtained from a strain of Flavobacterium and described in U.S. Pat. No. 4,039,384, are useful. Sarcosine oxidase can also be obtained commercially from a number of sources (e.g., Sigma, St. Louis, Mo.).

The use of a particular peroxidative substance such as HRP is not critical to the invention. A peroxidase is an enzyme which will catalyze a reaction wherein hydrogen peroxide oxidizes another substance. The peroxidases are generally conjugated proteins containing iron porphyrin. Peroxidases occur in horseradish, potatoes, fig tree sap and turnips, milk and white blood cells. They also occur in micro-organisms and can be produced by fermentation. Certain synthetic peroxidases are also known. Peroxidase, in particular HRP, is a preferred peroxidative substance, but other substances which are not enzymes are also useful. Many of these are commercially available (e.g., Sigma, St. Louis, Mo.). Suitable HRP substrates include 4-chloronaphthol, DAB, tetramethylbenzidine (TMB), 4-chloronapthol/MBTH, 3,5-dichloro-2-hydroxybenzene sulphonic acid/4-aminophenazone.

In addition, other compounds can be used as dyes in such reactions. For instance, imidazole leuco dyes are generally colorless in the leuco form, but are oxidized to a detectable colored dye in the presence of hydrogen peroxide and a peroxidative substance. Useful leuco dyes include di- and triarylimidazoles.

Many assays use various tetrazolium salts which are generally colorless in the oxidized form, but are reduced to a formazan, which is a detectable colored dye. Useful tetrazolium salts include nitro blue tetrazolium (NBT), tetranitroblue tetrazolium (TNBT), tetrazolium blue, tetrazolium red, tetrazolium violet, and the like. Other compounds which produce colored precipitates in the reduced form are well known to those of skill in the art. Such compounds include for example, diazonium and tetrazonium salts.

Enzyme activities are commonly measured using International Units (I.U.). For a given enzyme, one I.U. is defined as being the amount of enzyme activity required to catalyze the conversion of 1 micromole of substrate per minute under standard pH and temperature conditions for the enzyme. For the preferred enzyme preparations used in this invention, these standard conditions are 30° C. and pH 8.0 for creatininase, 37° C. and pH 7.4 for creatinase, 37° C. and pH 7.4 for sarcosine oxidase and 25° C. and pH 7.0 for peroxidase.

Creatinine assays can also be adapted for using color distance as a measure of concentration. In these assays, the immobilized enzyme in the detection zone, e.g., sarcosine oxidase is present across the detection zone. As the sample comprising sarcosine (derived from enzymatic conversions of creatinine in the sample) moves across the detection zone, the sarcosine is converted by an enzyme (e.g., sarcosine oxidase) to a product which ultimately produces a detectable color precipitate. The distance the color travels will be proportional to the concentration of creatinine in the sample applied to the device. Using the level of creatinine determined above, the estrogen concentration can be adjusted according to standard calculations.

Immunoassays and related assays can also be used to determine creatinine levels in a sample. As in the case of steroid hormone assays, a variety of labels may be employed in the devices. The labelling zone may contain labeling complexes that specifically bind to creatinine in the sample. The labeling complexes are often an anti-creatinine immunoglobulin bound to a visible label. The capture zone often contains an immobilized creatinine conjugate. The immobilized creatinine competes with creatinine in the sample for binding to labelled anti-creatinine antibodies following the same principles used for detection of steroid hormones. The assay strips may also comprise labelled creatinine wherein the labeled creatinine competes with creatinine in the sample for binding to a creatinine binding substance (e.g., antibodies) in a capture zone.

One of skill will recognize that variations on such immunoassays may be used. For instance, instead of a first anti-creatinine immunoglobulin, creatinine bound to colored beads may be used. In this assay, the creatinine in the sample will compete with the creatinine on the colored bead for binding to the immobilized anti-creatinine antibody in the capture zone. Thus, the amount of color detected on the assay strip will be inversely proportional to the amount of creatinine in the sample. Typically, the colored beads will be also be coated with a second protein, such as bovine serum albumin to prevent non-specific binding to the beads.

The accumulation of visible label may be assessed either visually or by optical detection devices, such as reflectance analyzers, video image analyzers and the like. The accumulation of visible label can be assessed either to determine the presence or absence of label in the capture zone or the visible intensity of accumulated label which may by correlated with the concentration or titer (dilution) of target analytes in the patient sample. The correlation between the visible intensity of accumulated label and analyte concentration may be made by comparison of the visible intensity to a reference standard. Optical detection devices may be programmed to automatically perform this comparison by means similar to that used by the Quidel Reflective Analyzer, Catalog No. QUO801 (Quidel Corp., San Diego, Calif.). Visual comparison is also possible by visual evaluation of the intensity and a color key such as used in the Quidel Total IgE Test Catalog No. 0701 (a multi-step ELISA assay). Thus, target analyte concentration in the sample may be determined. When the sample has been diluted to reduce viscosity and facilitate flow, appropriate correction of the measure concentration will be required. Video analyzers may also be used to determine the concentration of target analyte in the sample from the intensity of the accumulated label.

The geometric configuration of the devices of the present invention is not critical and may vary. Generally, the assay strips, and positive and negative control strips, if present, extend radially from the sample receiving zone at equally spaced intervals. The number and dimensions of assay strips and control strips in each device may also vary depending on the use.

The devices of the present invention may include housings that contain the matrixes. The housings are typically constructed of plastic, but other materials such as vinyls, nylons, or the like may be used. The housings have a top plate covering the assay surface of the matrixes. The top plate has a means for transmitting the sample to the matrix. Generally, the transmitting means is a sample well that is an opening in the top plate. The sample well is located over the sample receiving zone. The top plate also has a means for observing accumulation of label in the detection or capture zone following application of the sample. Typically, the observation means are result windows in the top plates. The result windows are located over the detection or capture zones of the assay strips on the matrix. Generally, the result windows are open, but the windows may be covered by a transparent covering such as glass or plastic. The housings may also contain dividers between the assay strips to inhibit flow of sample between assay strips.

The top plates may have a variety of configurations. In devices for simultaneous detection of creatinine and a steroid hormone, a single sample well and a plurality of result windows (one for each assay strip) are present. If the matrix has control test strips, result windows are located over the capture zones of the control test strips. A control sample well is located over the second sample receiving zone, when present.

Referring now to FIG. 1, an assay strip 10 is illustrated. This assay strip 10 has three components, a sample pad 12, a reagent pad 14, and an detection strip 16. The sample pad 12 and reagent pad 14 are preferably made from SONAT-ARA™ spunlaced 100% acrylic fiber (Dupont). The detection strip 16 is preferably nitrocellulose.

The sample pad 12 should also have means for eliminating potentially interfering substances from the sample. Depending upon the particular assay, different compounds are used for this purpose. For instance, as noted above for detection of estrogen, antibodies can be used to eliminate interfering cellular components. In the case of creatinine assays, if sarcosine oxidase is used in the assay, this enzyme may be included in the sample pad 12. Sarcosine oxidase in the sample pad 12 will remove N-ethylglycine which is also substrate for sarcosine oxidase and thus may artificially increase signal from the sample. In addition, if creatinine is converted to creatine in the assay (e.g., in a reaction catalyzed by creatinase), immobilized anti-creatine antibodies on the sample pad can be used to remove endogenous creatine in the sample. The enzymes and antibodies used to remove interference are preferably placed on beads (typically at least about 1 $\mu$m in diameter).

The sample moves by lateral flow to the next zone on the assay strip 10, the reagent pad 14. Again, the particular reagents placed on the reagent pad 14 will depend upon the particular assay being used. As noted above one assay suitable for detection of creatinine are those which convert creatinine to creatine, creatine to sarcosine, and sarcosine to glycine+formaldehyde+hydrogen peroxide. In these assays, creatininase, creatinase and an appropriate HRP substrate are placed on the reagent pad 14. Sarcosine oxidase and HRP are immobilized on the detection strip 16. As the sample flows through the sample pad 12, creatininase and creatinase convert creatinine in the sample to sarcosine. In addition, the sample picks up the HRP substrate on the reagent pad 14. When the sarcosine in the sample reaches the sarcosine oxidase in the detection strip 16, the hydrogen peroxide resulting from the conversion of sarcosine in combination with the HRP and its substrate result in a colored precipitate which is then detected.

A second suitable format uses the same elements on the sample pad 12, but includes creatininase, creatinase, NAD(P), and a tetrazolium salt on the reagent pad 14. In this embodiment, sarcosine dehydrogenase is immobilized on the detection strip 16. This enzyme converts sarcosine to glycine, formaldehyde and reduced NAD(P), NAD(P)H. The NADP(H) reduces the tetrazolium salt to produce a formazan, which is detected calorimetrically.

A third embodiment uses immunoglobulins or other creatinine binding substances to detect creatinine in the sample. In these embodiments, non-migratable anti-creatine antibodies on white beads ($\geq$ $\mu$m in diameter) are placed on the sample pad 12. Thus, non-specific levels of creatine are removed in the sample pad 12. The reagent pad 14 includes creatinine and bovine serum albumin (BSA) immobilized on colored beads (0.1–0.6 $\mu$m in diameter). The detection zone 16, includes immobilized anti-creatinine antibodies. Creatinine is detected by detecting colored beads in the detection zone 16. Creatinine in the sample and the creatinine-BSA coated beads will compete for binding to the antibodies in the detection zone 16. Thus, the amount of color detected will be inversely proportional to the creatinine level in the sample.

A fourth assay format relies on the use of creatinine:NAD(P) oxidoreductase and NAD(P). In this format, the sample pad 12 includes NAD(P), the reagent pad 14 includes a tetrazolium salt and the detection zone includes creatinine:NAD(P) oxidoreductase.

The following discussion describes devices suitable for the detection of steroids and hormones and urinary proteins and the correction of the results using creatinine levels detected in the sample. In particular, the devices are suitable for detecting estrogens and metabolites for the diagnosis of fertility status and urinary proteins for bone resorption or bone deposition. Generally, these devices provide means for determining creatinine levels to determine whether the sample is sufficiently concentrated to provide a reliable measure of urinary estrogen.

Figure 2:
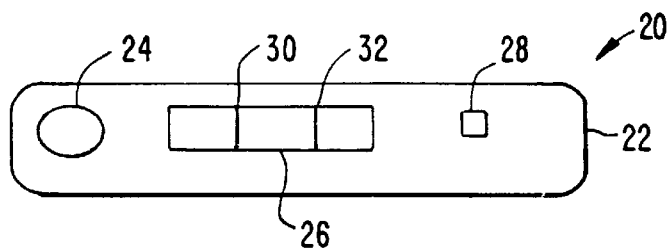
FIG. 2 illustrates a device constructed in accordance with the principles of the invention.

FIG. 2 shows a device 20 of the invention which provides creatinine correction by determining whether creatinine levels are above a predetermined threshold level. As noted above, the devices of the present invention may include housings that contain the matrixes. As illustrated in FIG. 2, the device 20 has a top plate 22 covering the assay surface of the assay strip(s). The top plate 22 has a means for transmitting the sample to the matrix. Generally, the transmitting means is a sample port 24 that is an opening in the top plate. The sample port is located over the sample pad of the appropriate assay strip. The top plate 22 also has a means for observing accumulation of label in each capture or detection zone following application of the sample. Typically, the observation means are one or more observation ports in the top plate 22 located over the capture zones of the assay strip(s) in the device 20. In the embodiment shown in FIG. 2, a first observation port 26 is used for detection of estrogen levels, and a second observation port 28 is used for determination of creatinine levels. Generally, the observation ports 26 and 28 are open, but the ports may be covered by a transparent covering such as glass or plastic. The housings may also contain dividers between the assay strips to inhibit flow of sample between assay strips.

The first observation port 26 is used to observe color on a test line 30 and a procedural control line 32. The procedural control line 32 is used to insure proper functioning of the device. The procedural control line 32 is located downstream of the test line 30 in the capture zone of the assay strip for detection of estrogen. A compound which will specifically bind the labelling complexes used in the assay but not specific for estrogen is immobilized on the procedural control line. As the sample containing label flows through the capture zone, it will contact the procedural control line 32. Through use of a ligand/anti-ligand reaction (e.g., biotin/avidin) solubilized label will be retained at the procedural control line 32 producing a detectable signal. Because the procedural control line is located downstream from the test line 30, accumulation of label on the procedural control line indicates that the sample has flowed through the capture zone and that the device is functioning properly.

The test line 30 is used to detect the target hormone according to the methods described above. In the simplest case, as estrogen levels rise, color will diminish on the capture line. In one embodiment, color keys based on samples containing known estrogen levels can be used. Exemplary color keys are shown in FIG. 3B, infra.

Creatinine levels are determined using the second observation port 28. Color will appear in the observation port 28 only if a predetermined threshold level of creatinine is present in the sample. Thus, the user can quickly and easily determine if the urine sample is sufficiently concentrated to provide reliable results.

A number of methods can be use to provide detectable color only if a minimum threshold level of analyte is present. For instance, anti-creatinine antibodies may be immobilized on the assay strips, preferably on the sample pad or reagent pad. The amount of antibody is selected so that if less than the desired threshold level of creatinine is present in the sample, all creatinine will be captured by the antibodies and insufficient levels of creatinine will remain to react with reagents on other downstream areas of the assay strip to produce detectable color. Alternatively, if the level of creatinine is greater than the predetermined threshold, sufficient creatinine will be available to react with the reagents on other downstream areas of the strip and produce detectable color in the observation port 28.

Figure 3A:
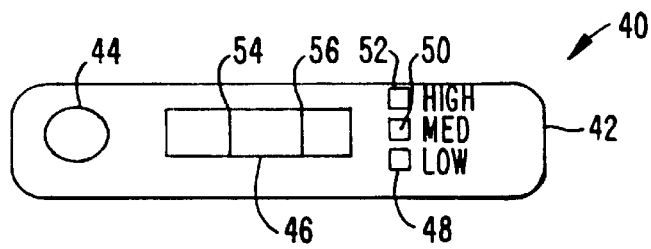
FIG. 3A illustrates a device constructed in accordance with the principles of the invention.
Figure 3B:
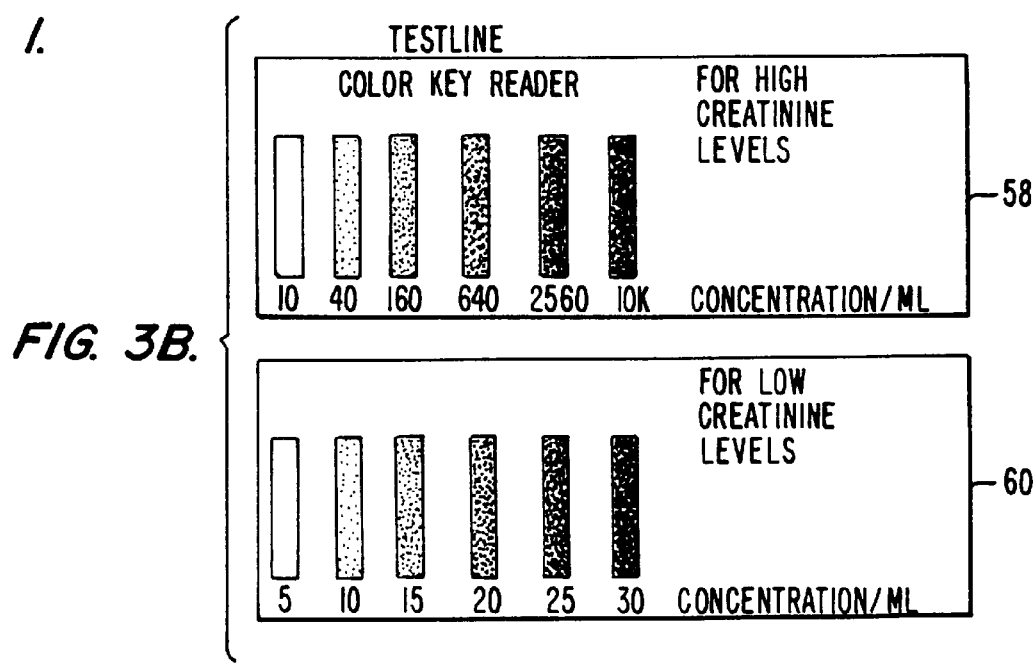
FIG. 3B illustrates a color key used with the device illustrated in FIG. 3A.

Alternatively, as shown in FIG. 3A, a device 40 has a top plate 42 covering the assay surface of assay strip(s). As in the previous embodiment, the top plate 42 has a sample port 44 that is an opening in the top plate. The sample port 44 is located over the sample pad of the appropriate assay strip. The top plate 42 also has observation ports in the top plate 22 located over the capture zones of the assay strip(s). A first observation port 46 is used for detection of estrogen levels, and observation ports 48, 50, and 52 are used for determination of creatinine levels.

As in the previous embodiment, the first observation port 46 is used to observe color on a test line 54 and a procedural control line 56. In this embodiment, however, creatinine threshold levels are selected at two or more levels. In this case three different levels, low, medium and high are selected. These creatinine zones also function as end of assay indicators. Creatinine levels are determined by reading the highest creatinine observation port (either 48, 50, or 52) that has color. Using this information, the estrogen levels are determined using different color key readers 58 or 60 as shown in FIG. 3B. Creatinine levels are also determined by the color key shown in 3B and the end-user mathematically corrects the estrogen value for creatinine based on a formula.

FIG. 4A shows a device 70 comprising a top plate 72 with a sample port 74 located over the sample pad of the appropriate assay strip. As in the previous embodiments, the top plate 72 also has observation ports located over the capture zones of the assay strip(s). A first observation port 76 is used for detection of estrogen levels, and observation ports 78, 80, and 82 are used for determination of creatinine levels.

In this embodiment, the observation port 76 reveals multiple test lines 84. The disappearance of a number of test lines 84 that show detectable color is correlated with the concentration of estrogen in the sample. In this embodiment, increasing levels of immobilized anti-estrogen antibodies are used at each test line 84 across the capture zone to facilitate capture. Indirectly labeled estrogen on the device competes with free estrogen in the sample for binding to these antibodies. As the sample flows through the capture zone, the detectable color will travel to a test line 84 at which all the indirectly labelled estrogen is completely bound. As the amount of free estrogen present in the sample increases, displacement of color will occur to lines further downstream.

Estrogen levels are then determined. FIG. 4B shows a sample concentration card 86 which can be used to determine estrogen levels using a the device shown in FIG. 4A.

As shown in FIG. 5, a device that detects and quantitates the target analyte assay for certain levels of creatinine in the sample may be used. Such devices rely on use of a conjugate of creatinine and target analyte, such as a carrier protein linked to creatinine and estrogen, attached to the same detecting label. Alternatively anti-hormone antibody or receptor and anti-creatinine antibody may be bound to the same label. In this case, capture zones comprising creatinine and the hormone analyte are used.

Methods for chemically coupling two proteins together are well known in the art. The particular method for constructing such conjugates is not critical to the invention, so long as the conjugate is capable of binding antibodies to the target analyte and antibodies to creatinine. If the conjugate comprises antibodies, the conjugate should bind both creatinine and the analyte. Generally linkers are either hetero- or homo-bifunctional molecules that contain a two reactive sites that may each form a covalent bond with the respective peptide. A number of linker molecules are well known to those of skill in the art. For example, the peptide monomers may be joined by a peptide linker, by a straight or branched chain carbon chain linker, or by a heterocyclic carbon. Heterobifunctional cross linking reagents such as active esters of N-ethylmaleimide have been widely used. See, for example, Lerner et al. (1981) *Proc. Nat. Acad. Sci.* (U.S.A.), 78: 3403–3407 and Kitagawa et al. (1976) *J. Biochem.* 79: 233–236.

FIG. 5 is a schematic diagram of an assay strip 90 of the invention. For the sake of clarity, the assay strip 90 is shown without the housing which includes a top plate comprising a sample port and observation ports generally as shown in FIG. 2. The assay strip 90 includes a sample zone 92 as described above and a label zone 94 comprising the labelled conjugate of creatinine and target analyte as described above. In the case of assays for estrogen, the label zone 94 may comprise estrogen and creatinine coupled to carrier protein bound to label. Sample placed on the sample zone 92 flows through the label zone 94. The capture zone 96 comprises two regions of immobilized capture agents. Anti-creatinine antibodies are immobilized in a first region 98. In the second region 100, anti-estrogen antibody, is immobilized. Usually, the first and second regions are in the form of lines which can be visualized through observation ports in the housing. The first second regions, need not be lines, however, and the capture agents can be arranged in the capture zone in other configurations as well. For instance, the two regions may each consist of a lawn of capture agents.

The amount of anti-creatinine antibodies in the first region 98 is so selected that if less than the desired level of creatinine is present in the sample, all detecting label will be captured and no detectable color will be seen further downstream in the capture zone 96. If the sufficient creatinine is present in the sample, the labelled conjugate flows to the second region 100. The amount of dually labelled creatinine/estrogen conjugate is adjusted so that target analyte above a certain level in the sample will bind to the antibody in capture zone 100 to displace the label to exhibit more color in the zone as analyte concentration increases. Therefore, if color appears in both regions, the test can be interpreted as being positive. If color appears only in the first region 98, the test is negative and the sample contains insufficient creatinine to determine analyte concentration.

In another embodiment shown in FIG. 6, a dual label assay for both the target analyte and creatinine relies on lawns of analyte binding substances (e.g., antibodies against the target analyte or creatinine) placed in two distinct capture zones. In this embodiment, an assay strip 110 of the invention includes a sample zone 112 as described above and a label zone 114 comprising the labelled conjugate of creatine and target analyte. The distance the creatinine and analyte (e.g., estrogen) label moves across the lawn is proportional to the concentration of first creatinine and then analyte in the sample. For instance, sufficient creatinine in the sample can be identified by determining if the dual label moves beyond one or more predetermined thresholds in the lawn of anti-creatinine antibodies (the first capture zone 116). As the level of creatinine rises, the degree of displacement of the label will increase indicating that the creatinine level is sufficient. Once the capacity of the anti-creatinine zone is exceeded by free creatinine, the label not bound to the creatinine-zone will spill over into the second capture zone 118 and show displacement relative to analyte concentration as above.

The approach described above can be used for any target analyte. Another example of an analyte for use in this assay format is pancreatic amylase. In this embodiment, antipancreatic amylase antibody and creatinine are attached to the same detecting agent. Monoclonal antibodies which specifically recognize human pancreatic amylase in the presence of abundant amounts of non-pancreatic amylase are commercially available from Oy Medix Biochemica Ab, Finland (clone code numbers 6101, 6104 and 6105).

In addition, the devices of the invention can contain multiple assay strips for the detection of one or more analyte in addition to a strip for creatinine correction. These embodiments allow for the simultaneous detection of different analytes and creatinine correction in a single sample. In such devices multiple assay strips are in fluid connection with a single sample pad. Such a device can have a number of configurations, but will typically be fan shaped with each assay strip extending radially from a single sample pad. A sample applied to the sample pad will flow into each assay strip resulting in detection of each target analyte. The assay strips may comprise any of the formats described above. For instance, a target analyte may be detected on an assay strip comprising a single test line and procedural control line, while creatinine is detected on an assay strip employing multiple test lines or on an assay strip for measure distance of detectable color.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A device for correcting a target analyte level in a fluid sample from a patient for a predetermined threshold level of creatinine, the device comprising:

a matrix defining an axial flow path, said matrix comprising:

a sample zone for receiving the fluid sample;

a label zone comprising a detection complex consisting essentially of a visible label, the target analyte, and creatinine, which are optionally coupled together by a linker; and a capture zone isolated downstream from the sample zone, the capture zone comprising a first region comprising a creatinine binding substance immobilized thereon and a second region comprising a target analyte binding substance immobilized thereon, said second region located downstream from said first reagion;

wherein the amount of the immobilized creatinine binding substance is selected such that if less than the predetermined threshold level of creatinine is present in the sample, all of the detection complex is immobilized in the first region and no visible label is seen in the second region.

2. The device of claim 1, wherein the target analyte is a urinary steroid.

3. The device of claim 1, wherein the target analyte binding substance is an immunoglobulin that specifically reacts with estrogen.

4. The device of claim 1, further comprising an absorbent zone located downstream from the capture zone.

5. The device of claim 1, wherein the first and second regions in the capture zone are lines.

6. A device for correcting a target analyte level in a fluid sample from a patient for a predetermined threshold level of creatinine, the device comprising:

a matrix defining an axial flow path, said matrix comprising:

a sample zone for receiving the fluid sample;

a label zone comprising a detection complex consisting essentially of a visible label, the target analyte binding substance, and a creatinine binding substance, which are optionally coupled together by a linker; and a capture zone located downstream from the sample zone, the capture zone comprising a first region comprising creatinine immobilized thereon and a second region comprising the target analyte immobilized thereon, said second region located downstream from said first regions wherein the amount of immobilized creatinine is selected such that if less than the predetermined threshold level of creatinine is present in the sample, all of the detection complex is immobilized in the first region and no visible label is seen in the second region.

7. A method of indicating if a predetermined threshold level of creatinine is contained in a fluid sample from a patient and for determining the amount of a target analyte in the same sample, the method comprising:

applying the sample to the sample zone of the device claimed in claim 1, and determining the amount of visible label present in the second region of the capture zone, wherein the amount of the visible label in the second region correlates to the amount of the target analyte in the sample and wherein the presence of the visible label in the second region indicates that the sample contains more than the predetermined threshold level of creatinine.

8. A method of indicating if a predetermined threshold level of creatinine is contained in a fluid sample from a patient and for determining the amount of a target analyte in the same sample, the method comprising:

applying the sample to the sample zone of the device claimed in claim 6, and determining the amount of visible label present in the second region of the capture zone, wherein the amount of the visible label in the second region correlates to the amount of the target analyte in the sample and wherein the presence of the visible label in the second region indicates that the sample contains more than the predetermined threshold level of creatinine.

* * * * *